(12) United States Patent
Bobic et al.

(10) Patent No.: US 11,513,310 B2
(45) Date of Patent: Nov. 29, 2022

(54) CYLINDRICAL ACTUATOR SUBASSEMBLY WITH FLEXURE-BASED LINEAR GUIDANCE MECHANISM

(71) Applicant: ACTUATOR SOLUTIONS GMBH, Gunzenhausen (DE)

(72) Inventors: Neven Bobic, Waiblingen (DE); Tobias Schumm, Fremdingen (DE)

(73) Assignee: ACTUATOR SOLUTIONS GMBH, Gunzenhausen (DE)

( * ) Notice: Subject to any disclaimer, the term of this patent is extended or adjusted under 35 U.S.C. 154(b) by 0 days.

(21) Appl. No.: 17/635,498

(22) PCT Filed: Oct. 1, 2020

(86) PCT No.: PCT/EP2020/077604
§ 371 (c)(1),
(2) Date: Feb. 15, 2022

(87) PCT Pub. No.: WO2021/064149
PCT Pub. Date: Apr. 8, 2021

(65) Prior Publication Data
US 2022/0342277 A1      Oct. 27, 2022

(30) Foreign Application Priority Data

Oct. 3, 2019  (IT) .......................... 102019000017843

(51) Int. Cl.
*G02B 7/04* (2021.01)
*G03B 1/00* (2021.01)
(Continued)

(52) U.S. Cl.
CPC ............ *G02B 7/04* (2013.01); *A61B 1/00188* (2013.01); *G03B 3/10* (2013.01); *G03B 13/36* (2013.01)

(58) Field of Classification Search
CPC . G02B 7/04; G02B 7/09; G02B 7/105; G02B 6/32; A61B 1/00188; A61B 1/00163; G03B 3/10; G03B 13/36
(Continued)

(56) References Cited

U.S. PATENT DOCUMENTS 11,226,469 B2 *   1/2022  Fan ........................ G03B 5/00
2004/0173445 A1   9/2004  Cole et al.
(Continued)

FOREIGN PATENT DOCUMENTS

CN        108088359 B       7/2019

OTHER PUBLICATIONS

International Search Report and Written Opinion dated Nov. 17, 2020 in PCT/EP2020/077604, 13 pages.
(Continued)

*Primary Examiner* — Marin Pichler
(74) *Attorney, Agent, or Firm* — Element IP, PLC

(57) ABSTRACT

A cylindrical actuator sub-assembly (100, 200, 300) comprising: an element (14, 24, 34) movable along a longitudinal axis (A), at least one actuating member and a guidance mechanism suitable for guiding the element, wherein aid guidance mechanism includes a first ring-shaped lever (11, 21, 31) and a second ring-shaped lever (11', 21', 31') that are parallel to each other, at least two straight axial flexures (12, 12'; 22, 22'; 32, 32'), at least two flexures (16, 16'; 27, 27'; 36, 36') and at least two bases (13, 13'; 23, 23'; 33, 33'), a first base carrying the movable element.

15 Claims, 7 Drawing Sheets

(51) Int. Cl.
  *G03B 3/10*    (2021.01)
  *A61B 1/00*    (2006.01)
  *G03B 13/36*   (2021.01)

(58) Field of Classification Search
  USPC .................................. 359/823, 825, 210.1
  See application file for complete search history.

(56) References Cited

U.S. PATENT DOCUMENTS

| | | |
|---|---|---|
| 2013/0208369 A1 | 8/2013 | Lam |
| 2017/0052386 A1 | 2/2017 | Siegrist et al. |
| 2017/0068165 A1 | 3/2017 | Marsollek et al. |
| 2018/0052381 A1* | 2/2018 | Koepfer .................. G03B 5/00 |

OTHER PUBLICATIONS

Search Report and Written Opinion dated Mar. 5, 2020 in Italian Patent Application No. IT 201900017843, 7 pages.

\* cited by examiner

CYLINDRICAL ACTUATOR SUBASSEMBLY WITH FLEXURE-BASED LINEAR GUIDANCE MECHANISM

The present invention is inherent to a cylindrical actuator subassembly with a flexure-based linear guidance mechanism that finds particularly advantageous application when there is an element to be moved along a specific and well defined axis. More specifically, the actuator takes up a cylindrical space except for a smaller cylindrical space which is taken up by the element to be moved along the axis of the cylinder.

The actuator is typically meant to move an optical lens (e.g. in an endoscopic instrument or an autofocus module) but it may be used for any application where a cylindrical actuator is required. At least one actuating member (e.g. a shape memory alloy wire) is attached to a lever which provides a gain of the movement at the driven side of the actuator, but the guidance mechanism is also required to move the lens in a proper and precise manner. In fact, the lever provides a rotational movement around its fixed end such that a first translational component of said movement is used to move the lens along the cylinder axis, but the rotational movement also results in a second translational component in a direction perpendicular to the cylinder axis which must be limited as much as possible by the guidance mechanism.

Properly designed and optimized flexure-based guidance mechanisms for actuators may achieve high stiffness and load capacity while simultaneously essentially neutralizing the parasitic errors bringing them to a minimal degree, such as out-of-plan motion, tilting errors and crosstalk. Among the above features, the minimization of parasitic errors in such a way as to not affect system performance and reliability is of key importance in applications such as autofocus camera modules, optical lens movement in endoscopic instruments, syringe actuators, cylindrical valves actuators.

The most common use of flexures in actuators and microactuators is simply as restoring force opposing a movement imparted by an actuating member, or as biasing means. One of the most recent fields exploiting this behavior is camera module control as exemplified in the international patent applications WO 2007113478, WO 2009056822, WO 2010012991 and WO 2019008522, the latter being in the applicant's name. As already mentioned, in all these documents the flexure role is passive, i.e. it does not cause the movement of a movable element (lens carrier) but reacts to it.

A flexure-based linear guidance mechanism is described in US 2018/0031088 describing the use of a set of four flexures to achieve linear displacement of an actuator plate, wherein each flexure is composed of two parallel flexure elements joined together and provided with pleats or arcs for an extension length. A first pair of flexures extend and are connected in a first direction between a base plate and an overlying actuator plate that are both L-shaped, while a second pair of flexures extend and are connected in a second direction between the base plate and the actuator plate, said second direction being perpendicular to said first direction. Such a guidance mechanism is quite bulky, since it also contains an electric motor as actuating member, and results in a parallelepipedal device.

Flexure-based actuators are also known from U.S. Pat. No. 9,651,772, describing an arrangement for actuation in an optical system relying onto two separate actuator units for paired flexures, that differently from the present invention aims at providing a tilting of optical elements rather than a linear displacement along a specific axis.

U.S. Pat. No. 7,239,107 describes the use of foldable flexures in the form of multi-bar linkages engaged by an actuator for x-y plane positioning adjustments, whereas the use of flat piezoelectric flexures in a parallelogram configuration is described in DE 4405501.

The paper "Tailoring Unconventional Actuators Using Compliant Transmissions: Design Methods and Applications" by Kota et al, published in IEEE/ASME TRANSACTIONS ON MECHATRONICS, VOL. 4, NO. 4, DECEMBER 1999 described the use of complex shape flexures in conjunction with electrostatic, piezoelectric, and SMA actuators for high precision applications (MEMS).

The purpose of the present invention is to provide a cylindrical actuator subassembly with a flexure-based linear guidance mechanism by making use of flexures having a simple structure and capable to cause displacement only along a pre-determined axis with essentially no spurious or secondary movement in any other direction. This purpose is achieved by means of a subassembly according to the main claim, while other advantageous features are recited in the dependent claims.

The invention will be illustrated with the help of the following non-limiting drawings, where:

In the above figure the dimensions of the represented elements are just for exemplary purposes and in some cases may have been be altered in order to improve the figures readability. Also, ancillary/accessory elements not necessary to understand the present invention such as, for example, actuating elements have been omitted in the figures for the sake of simplicity.

Figure 1:
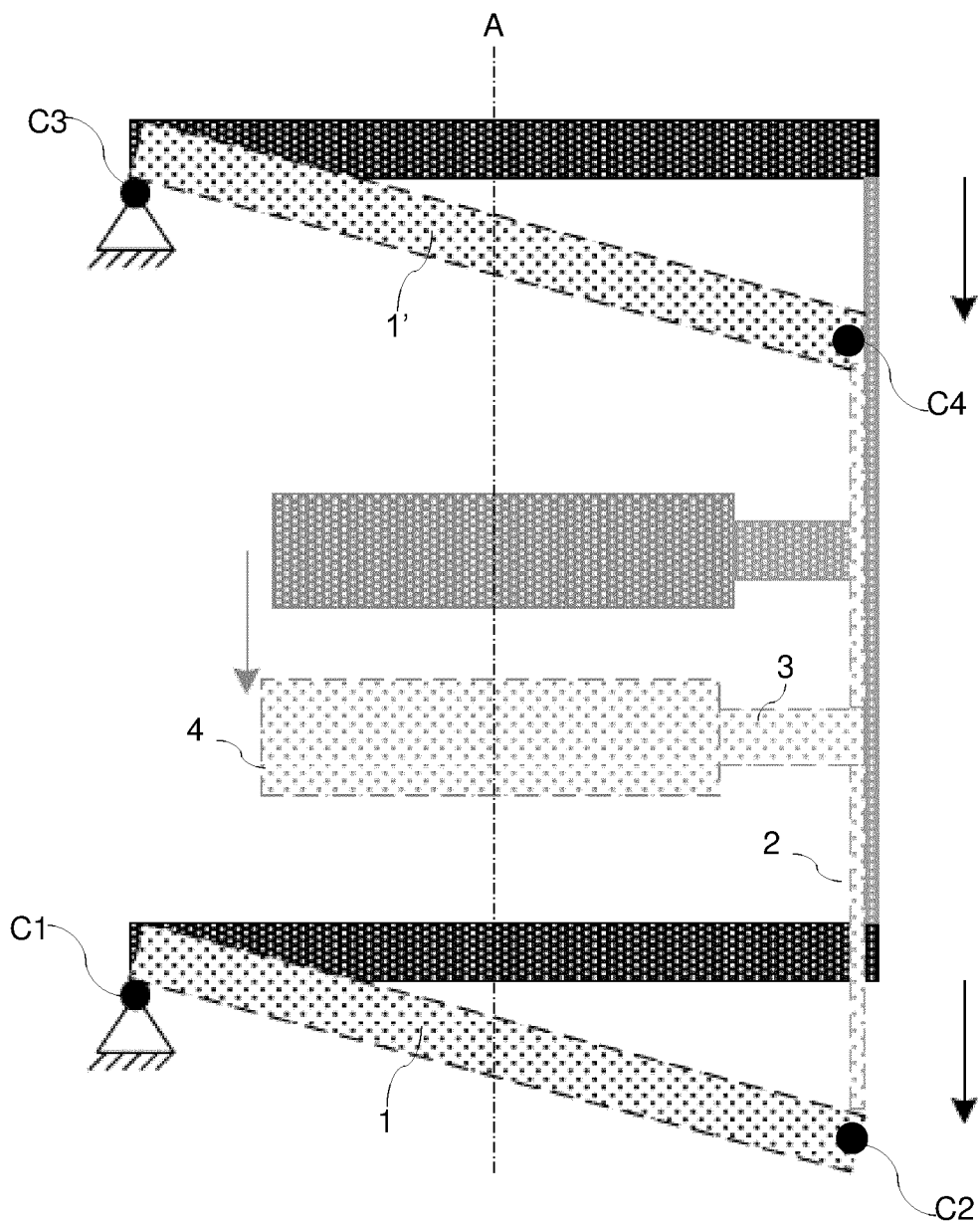
FIG. 1 shows a schematic diagram of a general double lever system integrated with a guidance mechanism for linearly moving a movable element.

Referring first to the diagram of FIG. 1, there is seen that the system includes a first lever arm 1 and a second lever arm 1' extending perpendicularly (in their rest position) to the longitudinal axis A of the cylindrical actuator subassembly. Said levers 1, 1' are fixedly pivoted at a first end and mutually connected at a free second end by an axial guidance member 2, that is provided with a transverse base member 3 on which a movable element 4 (runner) is mounted for a linear motion along said longitudinal axis A.

However, as previously mentioned, the rotation of levers 1, 1' also tends to move runner 4 in a transverse direction, that in the illustrated example is to the left since the levers are pivoted at their left ends. The two transverse lever arms 1, 1' form a virtual parallelogram with the axial guidance member 2, said parallelogram being flexible in its corners C1-C4 that represent virtual rotation points (black dots), of which points C1 and C3 are fixed whereas points C2 and C4 are mobile with the mobile sides of the parallelogram.

The driving force is provided by at least one actuating member (not shown) secured between a fixed position and one of the levers 1, 1' so as to generate an amplified stroke of the guidance member 2. The constructive challenge is to create a rotation point in a very small space and the solution provided in the present invention is the use of a flexure system including at least four flexures, each flexure being combined with another flexure and/or a lever to achieve a rotation point by forming an angle that ranges from 0° to 180°.

In particular, the perpendicular stiffness of the guidance mechanism (i.e. the resistance in a direction perpendicular to the direction of the axial movement of runner 4) is smallest for an angle of 0°/180°, which means that a movement of the levers in the transverse direction is also possible, whereas it is highest for an angle of 90°, which means that a movement of the levers in the transverse direction is almost not possible, and is obviously at an intermediate level for any angle value that is in between such as 45°/135°. In practice, the system preferably includes two axial flexures and two inclined flexures, namely two transverse flexures, i.e. at angles substantially equal to 90°, or two diagonal flexures, i.e. at angles substantially different from 90°.

Figure 2:
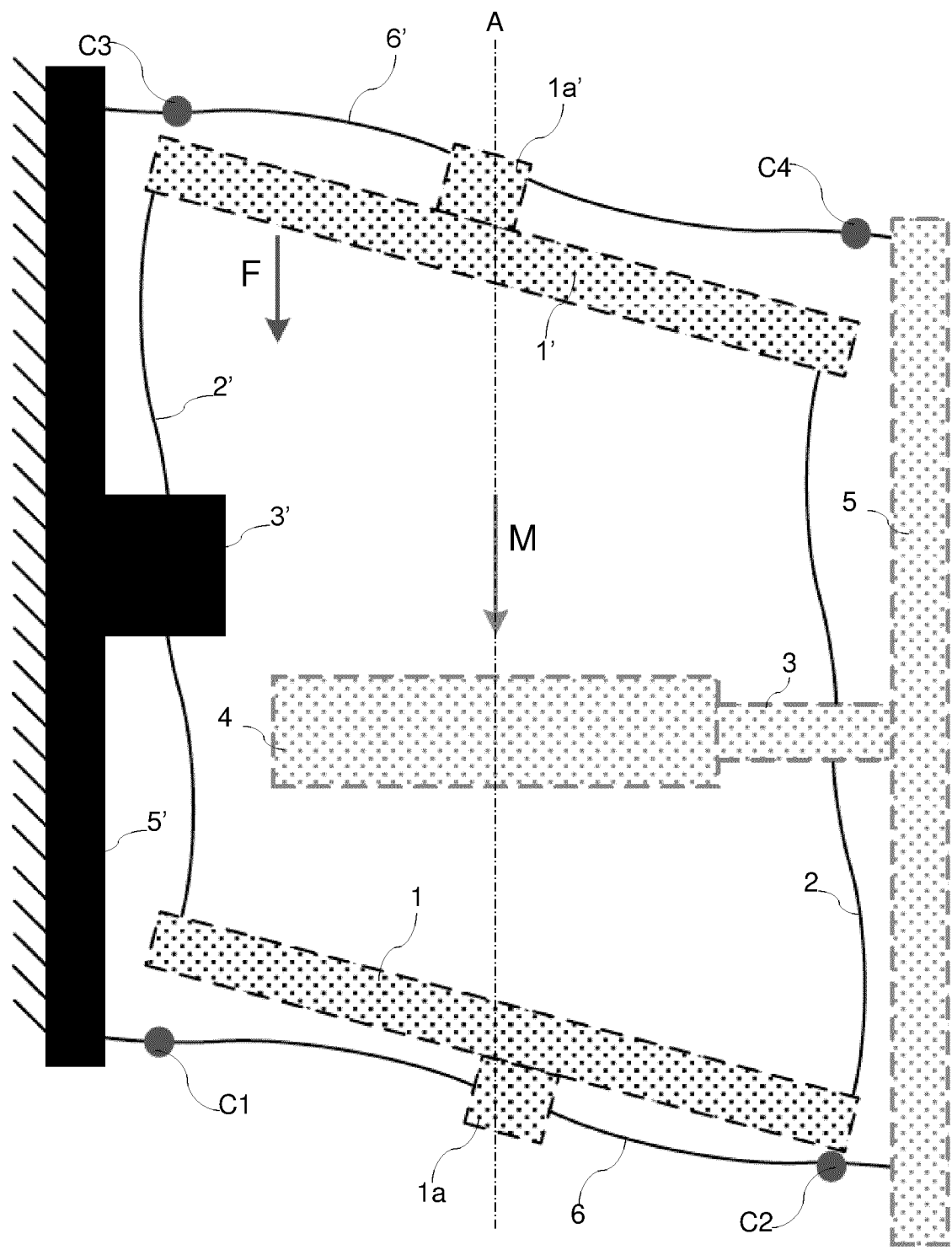
FIG. 2 shows a schematic diagram of a first embodiment of a guidance mechanism applied to a system of the type shown in FIG. 1.

The diagram of FIG. 2 shows a first embodiment of a guidance mechanism with 90° angles between the flexures (at rest) for maximum stiffness, such that the application of a force F to the second lever 1' results in a movement M of the movable element 4 that is substantially only axial, with a negligible transverse component in the direction perpendicular to axis A. In addition to the elements shown in FIG. 1, the diagram of FIG. 2 also shows that the guidance member 2 is a flexure, same as a second guidance member 2' and two transverse flexures 6, 6' that form angles of 90° with the axial flexures 2, 2' when in the rest position.

More specifically, the two axial flexures 2, 2' connect the two levers 1, 1' at the end portions thereof on their facing sides, said flexures 2, 2' being also respectively provided with a base 3 that carries runner 4 and with a corresponding base member 3'. Said bases 3, 3' are respectively connected at their radially distal ends to a mobile axial member 5 and to a fixed axial member 5'. The two transverse flexures 6, 6' connect the two axial members 5, 5' at the end portions thereof on their facing sides, said flexures 6, 6' passing also respectively through a holder 1a formed on the middle portion of the first lever 1 and a corresponding holder 1a' of the second lever 1'. The virtual rotation points C1-C4 are approximately located at the points of virtual intersection of flexures 2, 2' with flexures 6, 6' when the flexures are elongated, i.e. in the rest position.

While the lever parallelogram guidance mechanism is explained above in a two-dimensional way with reference to FIGS. 1 and 2, the available space in a cylindrical actuator has a cylindrical shape whereby a straight lever and a straight transverse flexure as shown in said figures are almost impossible, whereas the axial flexures may remain straight, therefore said levers and transverse flexures can be modified to take a ring shape.

Figures 3A, 3B, 3C:
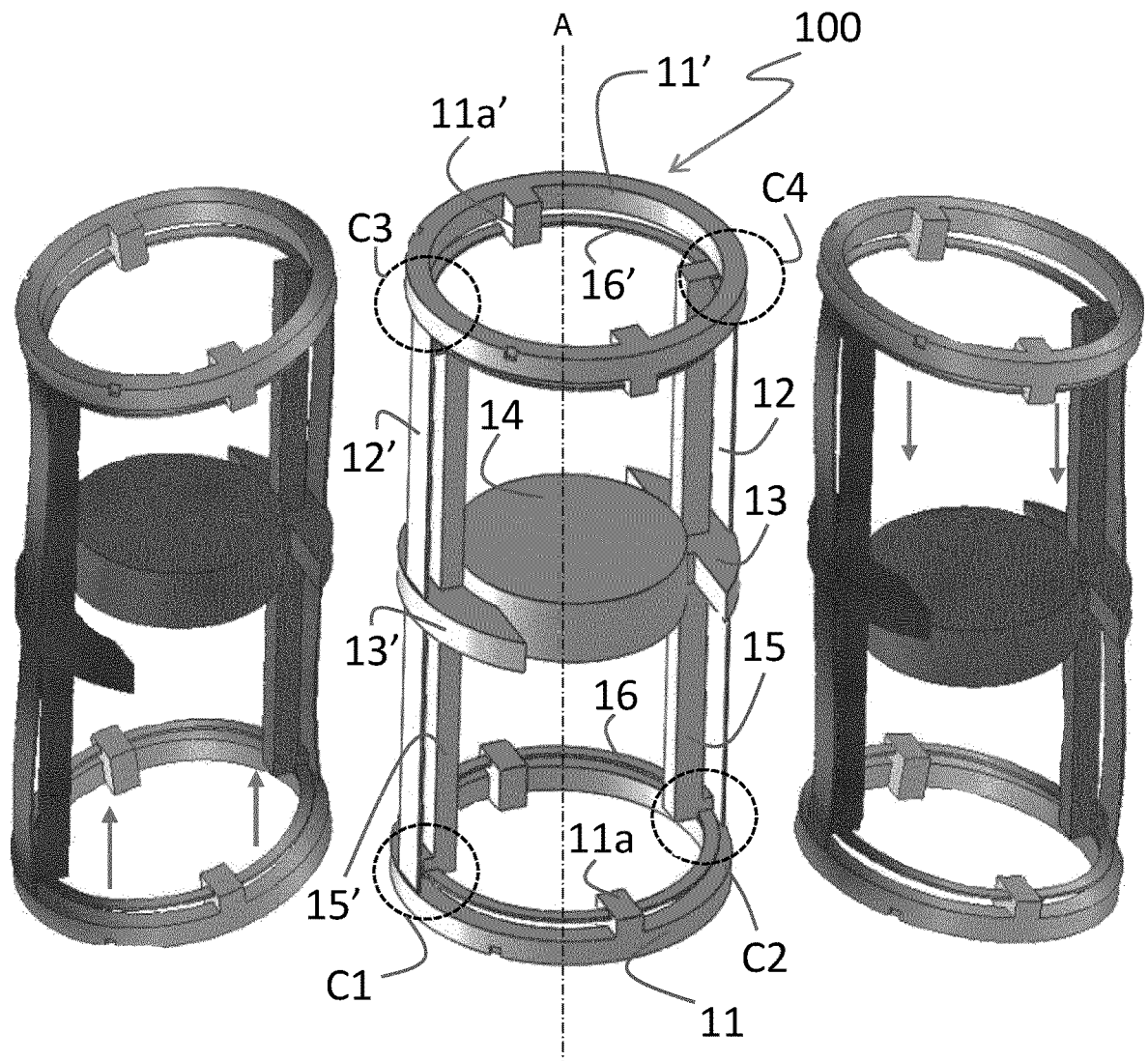
FIGS. 3A-3C show perspective views of a mechanism of the type shown in FIG. 2, in three different actuation states.

Such a three-dimensional arrangement is shown in the perspective view of FIG. 3A of a cylindrical actuator subassembly 100 according to a first embodiment of the present invention that substantially corresponds to the two-dimensional diagram of FIG. 2, except for the reverse positioning of the flexures with respect to the axial members and the levers and the subsequent size adaptation of the latter. In practice, a first ring-shaped lever 11 and a second ring-shaped lever 11' have an internal diameter and are axially spaced such that two axial members 15, 15' are comprised within the internal cylindrical space defined by levers 11, 11'.

In this way, two axial flexures 12, 12' connect the two ring-shaped levers 11, 11' at opposite peripheral portions thereof on their facing sides, said axial flexures 12, 12' being also respectively provided with bases 13, 13' through which said axial members 15, 15' are secured at radially internal positions with respect to the axial flexures 12, 12'. A movable element 14 is carried by base 13, and two ring-shaped transverse flexures 16, 16' extending parallel to the two ring-shaped levers 11, 11' connect the two axial members 15, 15' at the end portions thereof. Said transverse flexures 16, 16' pass also respectively through two holders 11a formed on opposite middle portions of the first lever 11 and through two corresponding holders 11a' of the second lever 11', the middle portions being defined as those equally spaced from the axial flexures 12, 12'.

Dotted circles C1-C4 represent the virtual rotation points defined between the straight axial flexures 12, 12' (parallel to the cylindrical actuator subassembly axis A) and the circular transverse flexures 16, 16' (at 90° angles with respect to said axis A in the rest position of FIG. 3A). It is important to underline that in this case the axial and inclined flexures do not contact each other but are anyway "coupled" to form the corners of the lever parallelogram, "coupled" meaning that the maximum radial distance between the straight axial flexures and the circular transverse flexures is not more than half of the radial distance between the axial flexures and the cylinder axis A (i.e. substantially half of the radius of the cylindrical actuator subassembly 100). Note that there is no minimum distance, i.e. actual contact between the axial and inclined flexures is possible.

In practice, the "coupling" points C1-C4 define a "virtual parallelogram" that by virtue of the bending (straight flexures 12, 12') or inclination (circular flexures 16, 16') of the flexures guides the movable element 14 into a substantially axial displacement when an actuating member causes the rotation of one of the ring-shaped levers as indicated by the arrows in the corresponding FIGS. 3B and 3C showing the system in different actuation states. More specifically, when one or more actuating members (not shown) have acted onto the first ring-shaped lever 11 or the second ring-shaped lever 11', the flexures guide the movable element 14 into respectively an axial upward (FIG. 3B) or downward (FIG. 3C) displacement.

It is important to remark that all the flexures 12, 12', 16 and 16' cooperatively and concurrently operate to guide the movable element 14, and that the median rest position of the latter shown in FIG. 3A is just the preferred configuration but such positioning is not mandatory.

Figure 4:
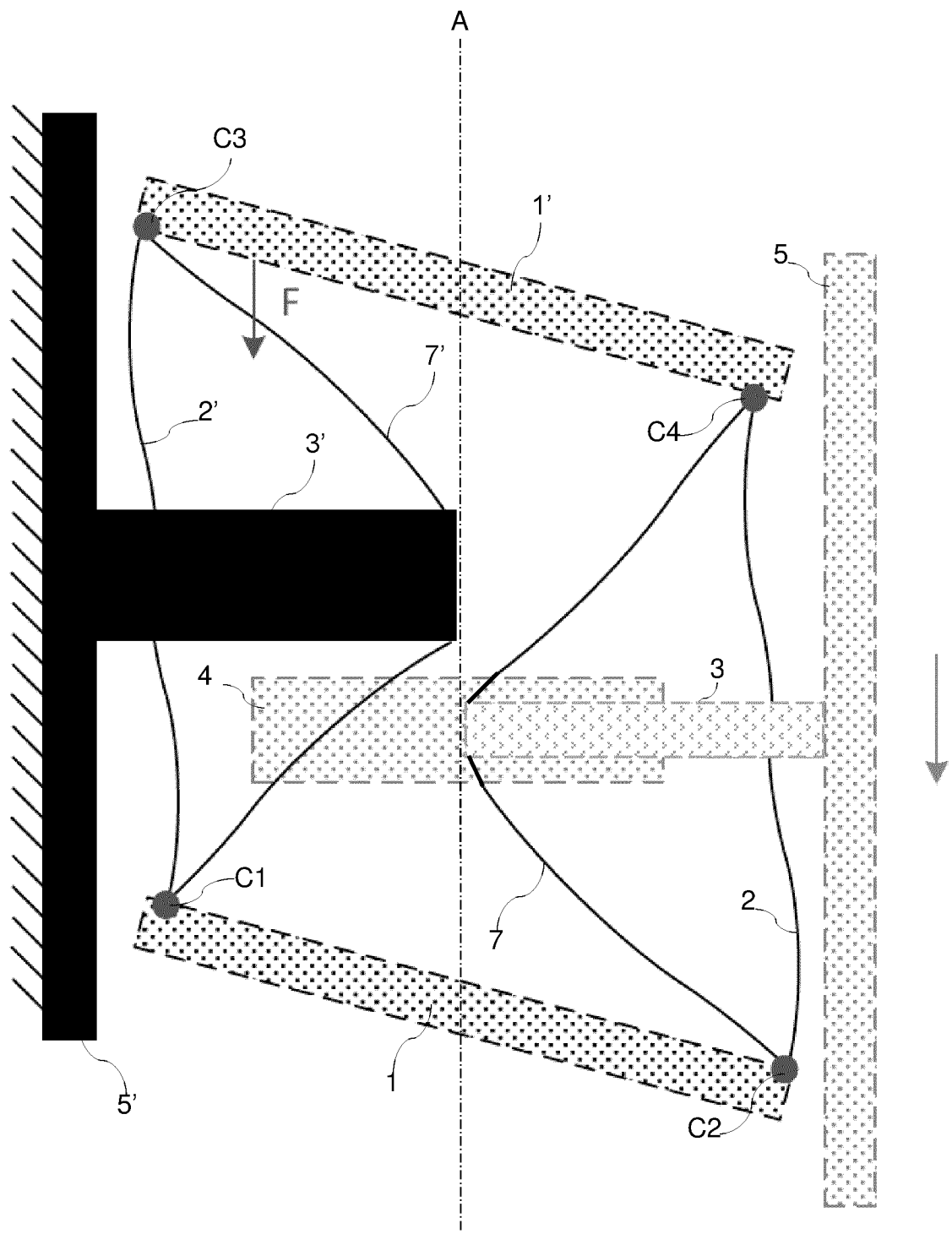
FIG. 4 shows a schematic diagram of a second embodiment of a guidance mechanism applied to a system of the type shown in FIG. 1.

The diagram of FIG. 4 shows a second embodiment of a guidance mechanism with 45° angles between the flexures (at rest), all four of which in this case extend between the two levers 1, 1' and are engaged by bases 3, 3' that have a much greater radial extension with respect to the diagram of FIG. 2. More specifically, the two axial flexures 2, 2' connect the two levers 1, 1' in the same manner as in the first embodiment described above in FIG. 2, whereas two diagonal flexures 7, 7' connect the two levers 1, 1' at the same points of the axial flexures 2, 2' but engaging bases 3, 3' at a radially internal end thereof that is close to the cylinder axis A. So the diagonal flexures 7, 7' have the same role of the circular transverse flexures 16, 16' of the previous embodiment, and they are subjected to the same "coupling" distance constraints to achieve the virtual rotation points C1-C4 that are located at the points of intersection of flexures 2, 2' with flexures 7, 7' where they connect at the ends of levers 1, 1'.

Figures 5A, 5B, 5C:
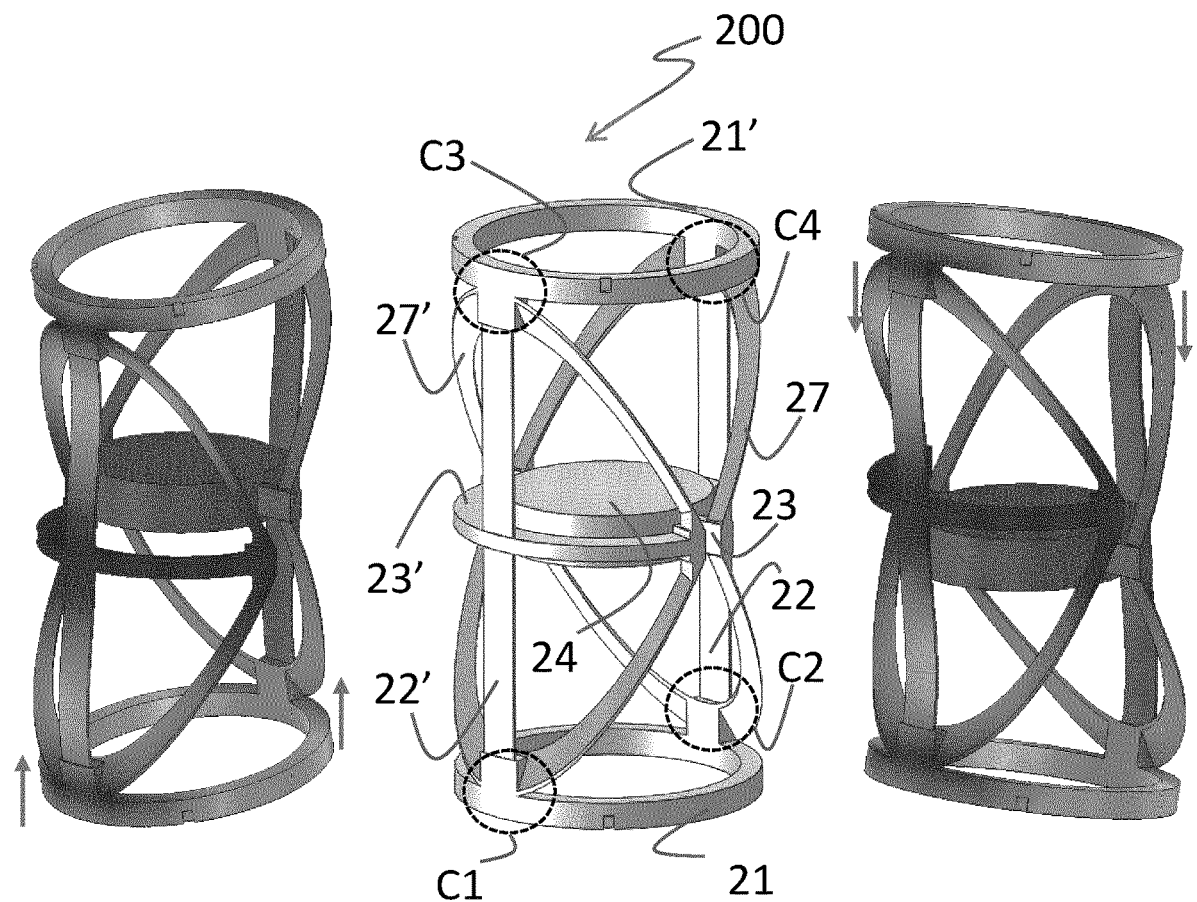
FIGS. 5A-5C show perspective views of a mechanism of the type shown in FIG. 4, in three different actuation states.

The three-dimensional arrangement shown in the perspective view of FIG. 5A of a cylindrical actuator subassembly 200 according to a second embodiment of the present invention substantially corresponds to the two-dimensional diagram of FIG. 4, except for the absence of the axial members. In practice, a first ring-shaped lever 21 and a second ring-shaped lever 21' have an internal diameter and are axially spaced such that a movable element 24 is comprised within the internal cylindrical space defined by levers 21, 21'. This movable element 24 is carried by a base 23 extending circumferentially to an almost semi-circular shape same as a corresponding base 23' on the opposite side of the mechanism, said bases 23, 23' extending symmetrically from two opposite axial flexures 22, 22' that connect the two ring-shaped levers 21, 21' at opposite peripheral portions thereof on their facing sides, similarly to the first embodiment shown in FIG. 3A.

Two elliptical diagonal flexures 27, 27' also connect the two ring-shaped levers 21, 21' at the same portions thereof, said diagonal flexures 27, 27' being also respectively engaged by bases 23, 23' but at the end portions thereof rather than at the middle portion where the axial flexures 22, 22' are located. As a consequence, the two halves of the diagonal flexures 27, 27' form angles of about 45° with the axial flexures 22, 22' but smaller angles could be formed by suitably changing the position at which the diagonal flexures 27, 27' are engaged by bases 23, 23'.

It is pointed out that the shape of the inclined flexures is preferably chosen from circular, linear, polygonal, elliptical or paired semi-elliptical, i.e. rather than being a closed ellipse it could also be made by two half ellipses individually extending between a lever and a base.

Similarly to FIG. 3A, also in FIG. 5A the movable element 24 is shown in a preferred but not mandatory median position and also in this case the coupling points C1-C4 define a "virtual parallelogram" that by virtue of bending (straight flexures 22, 22') or bending/inclination (elliptical flexures 27, 27') of the flexures guides the movable element 24 into a substantially axial displacement when an actuating member causes the rotation of one of the ring-shaped levers as indicated by the arrows in the corresponding FIGS. 5B and 5C showing the system in different actuation states. More specifically, when one or more actuating members (not shown) have acted onto the first ring-shaped lever 21 or the second ring-shaped lever 21', the flexures guide the movable element 24 into respectively an axial upward (FIG. 5B) or downward (FIG. 5C) displacement.

In brief, the cylindrical actuator subassembly according to the present invention incorporates a linear guidance mechanism with the following features:
- first and second ring-shaped levers that are parallel to each other and fixedly pivoted at a corresponding position,
- at least two straight axial flexures that are substantially parallel to the cylinder axis,
- at least two inclined flexures,
- at least two bases, one of which carries the movable element and is mounted either directly or indirectly on one of the at least two straight axial flexures.

The term "substantially parallel" in the context of the present invention shall be interpreted in a real environment sense, and it will encompass also elements with a negligible variation from the ideal definition of parallel, i.e. elements forming a ±5° angle.

As described above, the preferred embodiments include two opposite axial straight flexures, both substantially parallel to the cylinder axis, and two inclined flexures extending either transversely with a circular shape (FIG. 3A) or diagonally at 45° with an elliptical shape (FIG. 5A). However, as already mentioned, one or both of the elliptical flexures 27, 27' could be replaced by two half ellipses individually extending between a lever 21, 21' and a base 23, 23'. Similarly, also one or both of the circular flexures 16, 16' could be replaced by two half circles individually extending between an axial member 15, 15' and a holder 11a, 11a' whereby the total number of flexures could increase to five or six with any type of inclined flexures.

Such a modification could also be applied to one or both of the axial straight flexures 12, 12' or 22, 22' that could be replaced by two half flexures individually extending between a lever 11, 11' or 21, 21' and a base 13, 13' or 23, 23'. As a consequence, the combination of these possible modifications could increase the total number of flexures to any number between five and eight.

Conversely, the above-described four flexures could be combined into a smaller number of flexures with more complex shapes theoretically reducing the number of flexures even to one single flexure, whereby the guidance mechanism may include from one to eight flexures. Therefore, an essential feature of the present invention is the presence of at least eight flexure elements, defined as flexible elements extending between two rigid parts, that can be made as separate flexures with each flexure corresponding to a flexure element or combined into a smaller number of flexures with one or more flexures corresponding to a plurality of flexure elements.

For the sake of clarity in its definition, the present invention is described and claimed with reference to the preferred embodiment including at least four flexures, four being deemed the correct number which strikes a good balance between the cost and complexity in manufacturing and assembling the flexures. However, it is clear that any of the above-mentioned modifications to the number of flexures, as well as the addition of further flexure elements, falls within the scope of the present invention.

Figure 6:
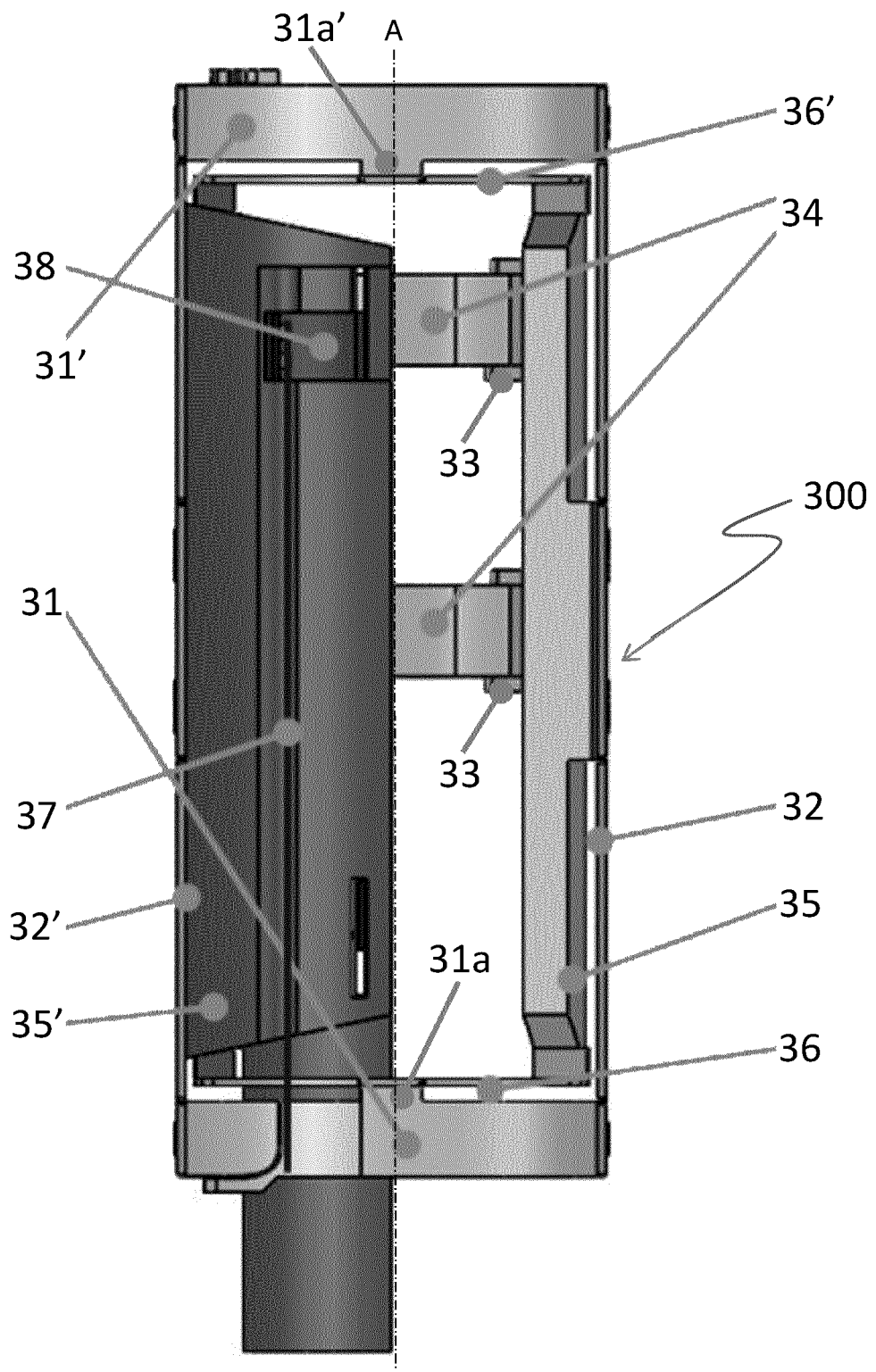
FIG. 6 shows a side view of an actuator subassembly for an autofocus camera module, incorporating a mechanism of the type shown in FIGS. 3A-3C.
Figure 7:
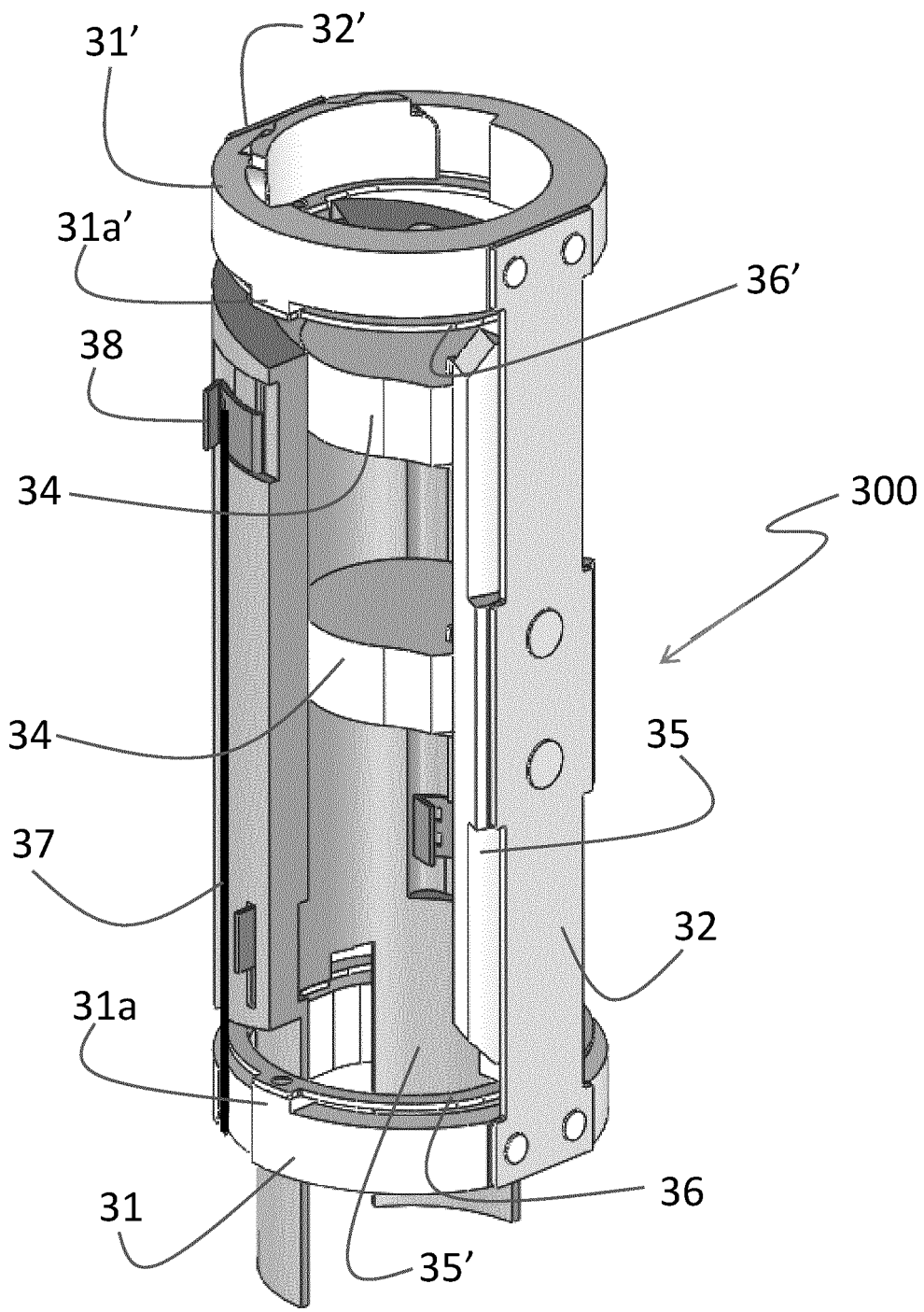
FIG. 7 shows a perspective view of the actuator subassembly of FIG. 6.

FIGS. 6 and 7 respectively show a side view and a perspective view of an actuator subassembly 300 for lenses focus regulation according to the first embodiment of the present invention, namely comprising a first ring-shaped lever 31 and a second ring-shaped lever 31' that have an internal diameter and are axially spaced such that two axial members 35, 35' are comprised within the internal cylindrical space defined by levers 31, 31'. Note that in this case the fixed axial member 35', differently from the fixed axial member 15' shown in FIGS. 3A-3C, extends axially beyond the first lever 31 and also circumferentially with a partial side wall up to the cylinder axis A, although in a further embodiment it might comprise a continuous side wall up to the mobile axial member 35.

Two axial flexures 32, 32' connect the two ring-shaped levers 31, 31' at opposite peripheral portions thereof on their peripheral sides, said axial flexures 32, 32' being also respectively connected to axial members 35, 35' at radially distal portions thereof. Two lenses 34 that make up a double movable element are carried by respective bases 33 which in this case are mounted on the mobile axial member 35, whereas the fixed axial member 35' has no base in this case. Two ring-shaped transverse flexures 36, 36' extending parallel to the two ring-shaped levers 31, 31' connect the two axial members 35, 35' at the end portions thereof, also passing respectively through two holders 31*a* formed on opposite middle portions of the first lever 31 and through two corresponding holders 31*a*' of the second lever 31'.

In the embodiment shown in these figures, the actuating member consists of a shape memory alloy (SMA) wire 37 that is secured between the first lever 31 and a crimp 38 that is externally mounted on the fixed axial member 35. It is to be underlined that the use of a SMA wire as actuating member is the preferred solution but the present invention is not limited to it, other suitable means including piezo-electric actuators and voice coil motors (VCM). The use of SMA wires, piezo-electric actuators and VCM as alternative and suitable means for driving the levers is known by a person skilled in the art and does not necessitate further explanation, as evidenced by the paper of Kota et al. already referenced in present application.

Similarly, it is clear that the actuator subassembly can include a plurality of actuating members at different positions, preferably in antagonistic configuration for a balanced actuation.

Although the present invention in not limited to a specific flexure material, preferred materials are aluminum, harmonic steel, superelastic nitinol and Ni—Ti based superelastic alloys including one or more of copper, titanium-copper alloys and flexible plastic materials.

The invention claimed is:

1. A cylindrical actuator subassembly having a longitudinal axis (A) and comprising:
    an element movable along said longitudinal axis (A);
    at least one actuating member suitable to cause the displacement of said movable element, and
    a guidance mechanism suitable to guide the movable element (14; 24; 34) in its displacement along the longitudinal axis (A) while minimizing any other type of movement,
    wherein said guidance mechanism includes:
        a first ring-shaped lever and a second ring-shaped lever that are parallel to each other and fixedly pivoted at a corresponding position along their periphery;
        at least two straight axial flexures that are substantially parallel to the longitudinal axis (A) and connect said first and second ring-shaped levers at opposite peripheral positions thereof, a first straight axial flexure being arranged at a position opposite to said fixed pivoting position of the ring-shaped levers so as to form therewith a virtual parallelogram flexible in its corners (C1, C2, C3, C4) that represent virtual rotation points, of which two rotation points (C1, C3) are fixed and two rotation points (C2, C4) are mobile along the direction of the longitudinal axis (A);
        at least two flexures that are inclined with respect to the longitudinal axis (A) and extend between two of said virtual rotation points (C1, C2, C3, C4); and
        at least two bases, a first base carrying the movable element and being mounted either directly or indirectly on said first straight axial flexure,
    wherein the radial distance at the virtual rotation points (C1, C2, C3, C4) between the at least two straight axial flexures and said at least two inclined flexures ranges from zero to half of the radial distance between the at least two straight axial flexures and the longitudinal axis (A), and
    wherein said at least one actuating member is secured between a fixed position and the first or second ring-shaped lever so as to exert a force in a direction parallel to the longitudinal axis (A) and at a position substantially close to the fixed pivoting position of the first and second ring-shaped levers, said force resulting in a movement of the two mobile rotation points (C2, C4) along the direction of the longitudinal axis (A) and a change of the inclination of the at least two inclined flexures with respect to the longitudinal axis (A).

2. The cylindrical actuator subassembly according to claim 1, wherein it further includes at least two axial members extending between the first and second ring-shaped levers and secured on said at least two bases or on the at least two straight axial flexures at a radially internal position with respect to the latter.

3. The cylindrical actuator subassembly according to claim 1, wherein the shape of one or more inclined flexures is chosen from circular, linear, polygonal, elliptical or paired semi-elliptical or paired semi-circular.

4. The cylindrical actuator subassembly according to claim 1, wherein the at least two inclined flexures are perpendicular to the longitudinal axis (A) and connected to the first or second ring-shaped lever through two holders formed on opposite middle portions thereof.

5. The cylindrical actuator subassembly according to claim 1, wherein the at least two inclined flexures form an angle of about 45° with the at least two straight axial flexures.

6. The cylindrical actuator subassembly according to claim 5, wherein the at least two bases extend circumferentially to an almost semi-circular shape and the at least two inclined flexures engage said bases at the end portions thereof.

7. An optical system comprising a cylindrical actuator subassembly according to claim 1.

8. A camera module or a medical diagnostic instrument, preferably an endoscope, that incorporates an optical system according to claim 7.

9. The cylindrical actuator subassembly according to claim 2, wherein the shape of one or more inclined flexures is chosen from circular, linear, polygonal, elliptical or paired semi-elliptical or paired semi-circular.

10. The cylindrical actuator subassembly according to claim 2, wherein the at least two inclined flexures are perpendicular to the longitudinal axis (A) and connected to the first or second ring-shaped lever through two holders formed on opposite middle portions thereof.

11. The cylindrical actuator subassembly according to claim 3, wherein the at least two inclined flexures are perpendicular to the longitudinal axis (A) and connected to the first or second ring-shaped lever through two holders formed on opposite middle portions thereof.

12. The cylindrical actuator subassembly according to claim 2, wherein the at least two inclined flexures form an angle of about 45° with the at least two straight axial flexures.

13. The cylindrical actuator subassembly according to claim 3, wherein the at least two inclined flexures form an angle of about 45° with the at least two straight axial flexures.

14. The cylindrical actuator subassembly according to claim 12, wherein the at least two bases extend circumferentially to an almost semi-circular shape and the at least two inclined flexures engage said bases at the end portions thereof.

15. The cylindrical actuator subassembly according to claim 13, wherein the at least two bases extend circumferentially to an almost semi-circular shape and the at least two inclined flexures engage said bases at the end portions thereof.

* * * * *